US010660805B2

(12) United States Patent
Kuo

(10) Patent No.: US 10,660,805 B2
(45) Date of Patent: May 26, 2020

(54) MATERIAL SAVING CLOTHING

(71) Applicant: Chien-Chung Chen, New Taipei (TW)

(72) Inventor: Shih-Huey Kuo, New Taipei (TW)

(73) Assignee: Chien-Chung Chen, New Taipei (TW)

( * ) Notice: Subject to any disclaimer, the term of this patent is extended or adjusted under 35 U.S.C. 154(b) by 581 days.

(21) Appl. No.: 15/475,155

(22) Filed: Mar. 31, 2017

(65) Prior Publication Data
US 2018/0207038 A1 Jul. 26, 2018

(30) Foreign Application Priority Data

Jan. 23, 2017 (TW) .............................. 106102401 A

(51) Int. Cl.
A61F 13/76 (2006.01)
A61F 13/58 (2006.01)
A61F 13/491 (2006.01)
A61F 13/66 (2006.01)
A61F 13/64 (2006.01)
A61F 13/49 (2006.01)
A61F 13/505 (2006.01)

(52) U.S. Cl.
CPC ........ A61F 13/76 (2013.01); A61F 13/49003 (2013.01); A61F 13/4915 (2013.01); A61F 13/505 (2013.01); A61F 13/58 (2013.01); A61F 13/64 (2013.01); A61F 13/665 (2013.01)

(58) Field of Classification Search
CPC .. A61F 13/76; A61F 13/505; A61F 13/49003; A61F 13/64; A61F 13/665; A61F 13/4915; A61F 13/58; A61F 13/62; A61F 13/15
See application file for complete search history.

(56) References Cited

U.S. PATENT DOCUMENTS

| | | | | |
|---|---|---|---|---|
| 3,420,236 A * | 1/1969 | De Woskin | ............. | A61F 13/76 604/396 |
| 3,635,221 A * | 1/1972 | Champaigne, Jr. | ... | A61F 13/505 604/364 |
| 4,955,880 A * | 9/1990 | Rodriquez | ............. | A41B 13/04 604/393 |
| 5,019,068 A * | 5/1991 | Perez | ...................... | A61F 13/66 604/386 |
| 2012/0116339 A1* | 5/2012 | Labit | ................. | A61F 13/49004 604/372 |

(Continued)

Primary Examiner — Tatyana Zalukaeva
Assistant Examiner — Gabriella E Burnette
(74) Attorney, Agent, or Firm — Leong C. Lei

(57) ABSTRACT

Disclosed is material saving clothing including a repeatedly usable general-purpose holding and looping member for replacement with a full-pad type or a partial-pad type absorbent article and an absorbent article. The holding and looping member has a rear waist portion that is provided with a rear opening and a rear clamp section and a front portion that is provided with a front opening and a front clamping section. The front portion is provided, on a lower portion of each of left and right sides thereof, with a side clamp section and anti-skidding glue. The absorbent article is provided, above a rear end thereof, with left and right rear pulling sections positionable into a rear opening and clamped (from opposite sides) by a rear clamp section and a front clamping section provided above a front end to be pulled through a front opening for clamping by a front clamping section.

15 Claims, 13 Drawing Sheets

(56) References Cited

U.S. PATENT DOCUMENTS

2014/0221954 A1\* 8/2014 Wang ................ A61L 15/40
                                                  604/385.14
2017/0007474 A1\* 1/2017 Kuo ................. A61F 13/76

\* cited by examiner

MATERIAL SAVING CLOTHING

(a) TECHNICAL FIELD OF THE INVENTION

The present invention relates generally to an absorbent article (such as paper diaper) and a holding and looping member thereof, for the purposes of reducing consumable material and improving environment protection and economics.

(b) DESCRIPTION OF THE PRIOR ART

For patients having different degrees of activity or different types of reliance, different types or replacement ways of diapers are different. Patients having lower body paralysis or total paralysis take around one half and to change diaper, the operation can only be conducted separately by respectively turning the body leftward and rightward. For patients of paralysis or using urinary catheters, front abdomen-side liquid absorbent core is generally unneeded and peripheral consumable material is also not necessary. However, modifying or reducing may face the difficulty that wearing may be impossible or tightness of attachment may not be achieved. As such, the already known shortcomings, such as excessive consumable material used, being expensive, sultriness, and poor skin attachment that leads to ready urine leakage, are still existing. In addition, installation of urine catheters may cause troubles such as displacing, entangling, and detachment.

SUMMARY OF THE INVENTION

To overcome the drawbacks of the prior art, the present invention provides a material saving clothing, wherein a holding and looping member tightly loops and holds an absorbent article closely against a human body to achieve reduction of material consumption to enhance environmental protection and economics, delaying or suppressing overflowing of waste product, allowing for alternative manipulation from left or right side, preventing skidding and entangling of a catheter, allowing for proper replacement of an absorbent article in the daytime and nighttime, and allowing for frontward and rearward movement for adjusting the site of absorption.

To achieve the above objective, a technical solution adopted in this invention is material saving clothing, which comprises a repeatedly usable general-purpose holding and looping member and an absorbent article. The following is a description of a person having a waist circumference length around 80 cm taking a standing posture after wearing as an example for description of direction, position, and size:

The holding and looping member is provided, on each of left and right ends of a rear waist portion, with an extendible/retractable section (allowing a toilet user easy to readily take off) and is externally connected to a pulling and holding band. A rear opening (which can be pulled open to receive left and right rear pulling sections to be positioned therein) is provided between the extendible/retractable sections, and a rear clamp section (for clamping and pulling up the left and right rear pulling sections) that is openable and closable by means of an internal layer and an external layer is provided above the rear opening. The rear clamp section is provided, on a front side thereof, with an attaching section of a soft woven surface (for improving comfortableness of the waist and also for attaching fastening). A front portion is provided with a front opening (allowing for ready withdrawal of the front pulling section outward for manipulation on the outside) and a front clamping section (shielding the front opening and clamping and lifting up the front pulling section). The front portion is provided on a lower part of each of left and right sides with a side clamp section that is openable and closeable by means of the internal layer and the external layer (for clamping and lifting up side wings of the front pulling section) and catheter anti-skidding glue (that provide flexibility and elasticity and does not detach even being kneaded).

Due to being general type, the front rear opening and the male-female fastener can be extended therethrough for clamping or alternatively being not used. The hook-and-loop fasteners can be used for attaching and fastening or skidding prevention, or for making a waist force receiving surface flat. The anti-skidding glue may prevent positional shifting of a front belly zone or a front pulling section. The holding and looping member may be used by other back adhesive type absorbent articles for tightly looping and being set against the body.

The absorbent article can be classified as follows:

(1) Full-pad type (first and second embodiments), wherein the absorbent core layer comprises a rear hip zone, a crotch zone, and a front belly zone and is suitable for being worn on a person that takes activities.

(2) Partial-pad type (the third embodiment to the modified seventh embodiment), wherein the absorbent core layer comprise a rear hip zone and a crotch zone, while a front belly zone is omitted, suitable fore being worn on a patient of paralysis or worn on a catheter wearing person during nighttime. The left and right rear pulling sections and the front pulling section can be displaced in a direction toward an upper belly portion and then fixed so that an absorbent section is frontward shifted to be suitable for wearing for sitting up or taking activity, making it saving material and preventing overflowing of waste product.

Characteristics of the full-pad type are that, in the first embodiment, the left and right rear pulling sections can be extended through a rear opening and then individually folded frontward for attaching and fixing to an attaching section or a rear hip zone so that a patient having strong intension for moving could be applied with further fastening through male-female fasteners. In the second embodiment, the left and right rear pulling sections may be positionable into a rear opening or being turned downward for folding and positioning in a rear clamp section to be fixed thereby. The front pulling section, after being withdrawn out through a front opening, can be clamped and pulled up by the front clamping section. The crotch zone is provided, on a location adjacent to each of left and right side edges, with a tight core top portion of a high density liquid absorbent layer that extends frontwards and rearwards (such that externally, the thickness is not increased and buffering may be achieved for urine to delay overflowing and enhancing absorption capacity).

Characteristics of partial-pad type are that a liquid absorbent layer of the front belly portion is omitted and a front end of a crotch zone is folded rearward to form a folded stop portion (wherein when the liquid absorbent layer absorbs liquid and bulges, the folded stop portion is expanded as a water barrier) such that, in other words, means including the tight core stop portion and the folded stop portion are provided on left and right sides and the front end of the crotch zone to prevent leaking of waste product. In the third to fifth embodiments, the front pulling section comprises a U-shaped notch having two end portions that can be pulled through a front opening and clamped and lifted up by a front clamping section such that the U-shaped notch allows a male regenerative organ to expose and return to being wrapped by soft and ventilating fabric (the holding and looping member), allowing for a catheter to extend out to contact anti-skidding glue.

Other embodiments of material saving for partial-pad type are as follows:

(1) Sixth embodiment 6 featuring back adhesive and the front pulling section comprising a cut-open slit (for use in wintertime) through which male or female catheter may be extended; and modified sixth embodiment 6' features enhanced back adhesive and the front pulling section having not opening or slit and requiring no formation of a folded stop portion (suitable for use by a patient having strong intension of moving in wintertime);

(2) Seventh embodiment 7 features the front pulling section comprising left and right side wings (where a male catheter may be extended across an upper side to contact with anti-skidding glue and a female catheter is prevented from moving when a user body is turned around); and modified seventh embodiment 7' features both back adhesive and the front pulling section comprising left and right side wings (for use by a patient carrying a catheter with strong intension for moving).

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 1-2 is a perspective view showing a rear clamp section of the absorbent article 1, and a partially broken view of a portion thereof taken in an opposite direction for better understanding.

FIG. 1-3 is a cross-sectional view taken of a tight core stop portion of the absorbent article 1 taken along line X1-X1 of FIG. 1-2.

FIG. 1-4 is a schematic view demonstrating an operation of left and right rear pulling sections at individual sides thereof.

FIG. 1-5 is a schematic view, taken from a front side, illustrating the absorbent article 1 in a condition of being worn.

FIG. 1-6 is a schematic view, taken from a lateral side illustrating the absorbent article 1 in the condition of being worn.

FIG. 2 is a perspective view demonstrating expansion of a full-pad type absorbent article 2 and a holding and looping member according to a second embodiment of the present invention.

FIG. 3-1 is a perspective view showing a partial-pad type absorbent article 3 according to a third embodiment of the present invention, indicating positioning directions of left and right rear pulling sections and being clamped and fixed and a front pulling section being clamped and fixed.

FIG. 3-2 is a cross-sectional view of a folded stop portion of the absorbent of the third embodiment taken along lien Y1-Y1 of FIG. 3-1.

FIG. 3-3 is a schematic view illustrating a condition before movement of an absorbent article 3 and a condition after the movement (where a bottom is lifted upward) for comparison and also illustrating a condition before being worn with a male catheter contacting anti-skidding glue.

FIG. 4 is a perspective view demonstrating expansion of a partial-pad type absorbent article 4 and a holding and looping member according to a fourth embodiment of the present invention.

FIG. 5-1 is a perspective view demonstrating a partial-pad type absorbent article 5 and a holding and looping member according to a fifth embodiment.

FIG. 5-2 is a schematic view illustrating a condition before movement of an absorbent article 5 and a condition after the movement (where a bottom is lifted upward) for comparison and also illustrating a condition before being worn with a female catheter as an example for contacting anti-skidding glue.

FIG. 6 is a schematic view demonstrating expansion of a partial-pad type absorbent article 6 and a holding and looping member according to a sixth embodiment, and illustrating locations where male and female catheters are positionable, and also illustrating a modified absorbent article 6' for reference and comparison.

DETAILED DESCRIPTION OF THE PREFERRED EMBODIMENTS

Figure 1:
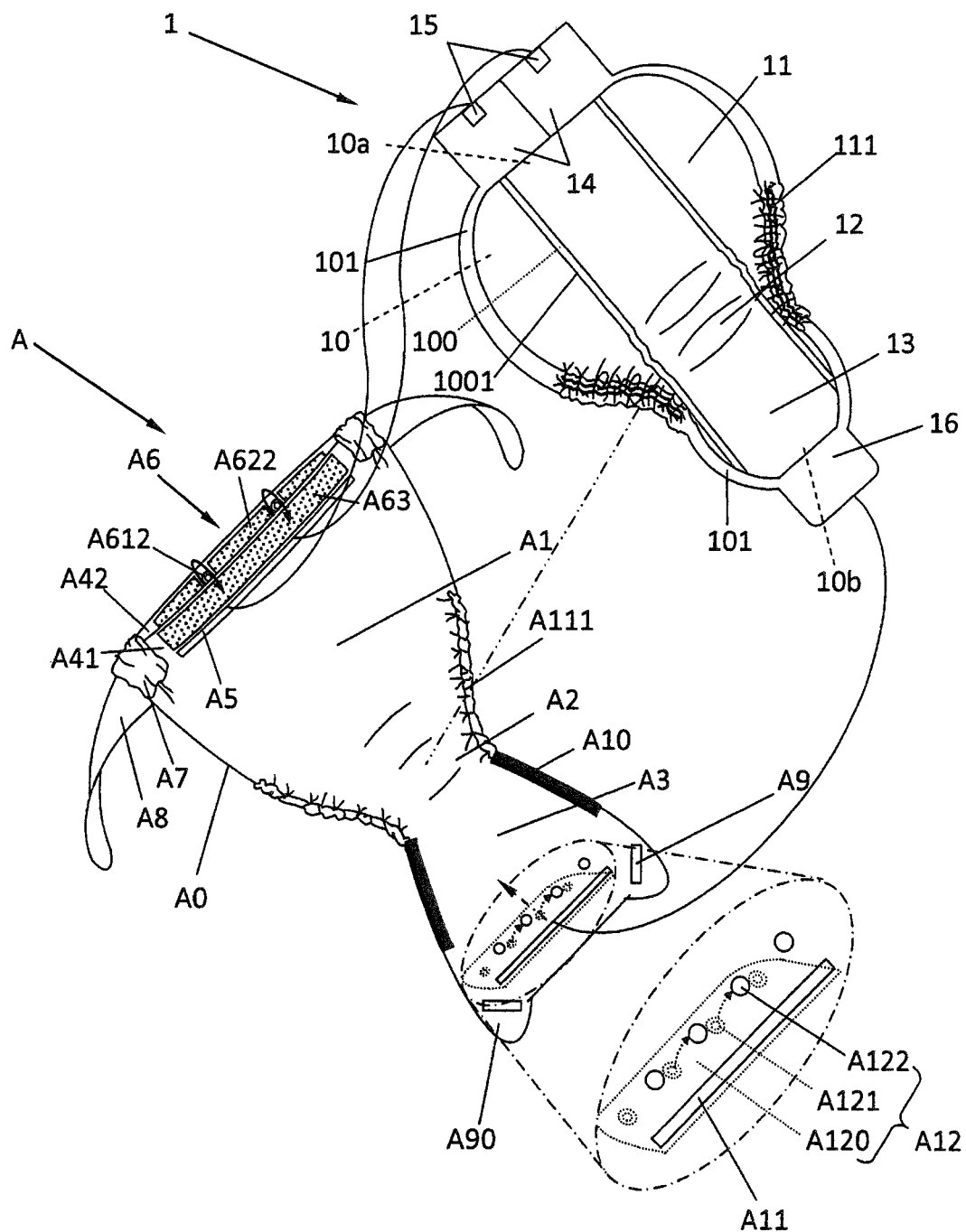
FIG. 1-1 is a perspective view demonstrating expansion of a full-pad type absorbent article 1 and a holding and looping member according to a first embodiment of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIGS. 1-1 to 1-6, a holding and looping member A and a full-pad type absorbent article 1 are provided, wherein the holding and looping member comprises a double-layered main body A0; provided on each of a left end and a right end of a rear waist portion is an extendible/retractable section A7 that comprises an elastic band arranged therein, and, coupled to each of outer ends thereof is a pulling and holding band A8, which has a front segment A81 that comprises a hook-and-loop fastening male portion A831 extending through a through hole A91 formed in a front portion and foldable rearwards to get fastening engageable with a rear segment A82 that comprises hook-and-loop fastening female portion A832 thereon (FIG. 1-5), wherein the rear segments are gradually widened in a direction toward the main body in order to enlarge a pulling and looping surface and spread out a force receiving surface and a pad sheet A90 is provided on an outer side of the through hole A9. Provided in an internal layer A41 between the extendible/retractable sections is a rear opening A5, and a rear clamp section A6 is provided above the rear opening for openably coupling the internal layer and an external layer A42. The rear clamp section is provided, in a manner of covering a front side thereof, with an attaching section A63 having a soft woven surface to which attachment can be made. The front portion A3 is provided, at a location corresponding to a portion between the pubic bone and the belly button, with a front opening A11 and a front clamping section A12. A shrinkage edge A111 is formed on each of a left side and a right side by providing an elastic band to each of left and right sides of a lower part of the rear portion A1 and associated left and right sides of a lower portion A2. Provided on each of a left side and a right side of a lower part of the front portion A3 is a side clamp section A31 (FIG. 7) that comprises at least one male-female fastener A311 mounted to surfaces of the internal layer and the external layer that face each other for openably coupling therebetween, and the internal layer is provided, through coating, with catheter anti-skidding glue A10 (FIG. 1-5) on a front side thereof at locations adjacent to each of a left lower edge and a right lower edge.

The rear clamp section is provided, on the internal layer, with female fastener parts A611 of two horizontally arranged male-female fasteners for corresponding to and coupling engagement with two male fastener parts A612 horizontally arranged on the external layer; and male portions A621 of three hook-and-loop fasteners provided on the internal layer and respectively arranged between the two female fastener parts and opposite left and right sides thereof and female portions A622 of the three hook-and-loop fasteners, which correspond to and are engageable with the male portions, provided on the external layer.

The front clamping section comprises a coupling lid A120 that shields the front opening and the coupling lid is provided, on the internal layer, with female fastener parts A121 of a plurality of horizontally arranged male-female fasteners, with male fastener parts A122 being provided on the front portion to be correspondingly to and engageable with the female fastener parts.

The absorbent article 1 is formed of a nonwoven surface layer, a waterproof bottom layer, and an absorbent core layer 10 interposed therebetween and comprises a rear hip zone 11, a crotch zone 12, and a front belly zone 13 over all of which the absorbent core layer 10 is distributed, and left and right rear pulling sections 14 and a front pulling section 16, wherein the left and right rear pulling sections are widthwise planar surfaces, which are respectively formed of two equal parts by bisecting a portion of a coupling film 101 that is approximately a quarter (¼) of a total waist circumference length and located above a rear end 10a of the absorbent core layer, and are each provided, on a middle of an upper edge thereof, with an adhering and attaching pad 15 to be fit into the rear opening A5, extending upward therethrough, and folded frontward to attach back to the attaching section A63 or the rear hip zone 11. The crotch zone 12 is provided, at a location adjacent to each of a left side edge and a right side edge thereof, with a tight core stop portion 100 of the high density liquid absorbent core layer 10, which is of a width that is about 1 cm and extend frontwards and rearwards, and is provided with an indentation line 1001 on each of left and right sides thereof. An extendible/retractable edge 111, which is formed of an elastic band, is provided on a portion of the coupling film that is located on a lower part of each of left and right sides of the rear hip zone and associated left and right sides of the crotch zone. The front pulling section 16 is formed, as a planar surface, by a portion of the coupling film that is located above a front end 10b of the absorbent core layer and is extendable through the front opening A11 and folded back downward to be fixed by the front clamping section A12.

As shown in FIG. 1-4, the body of a wearer M is turned leftward and a left half of the absorbent article 1 is first wound and then the rear opening A5 is pulled open to allow the left and right rear pulling sections 14 to be set therethrough. Afterwards, the right rear pulling section is turned frontward and gets attached. Then, the body is turned rightwards and the left half is expanded and the left rear pulling section is turned frontward and gets attached.

Figures 1, 2:
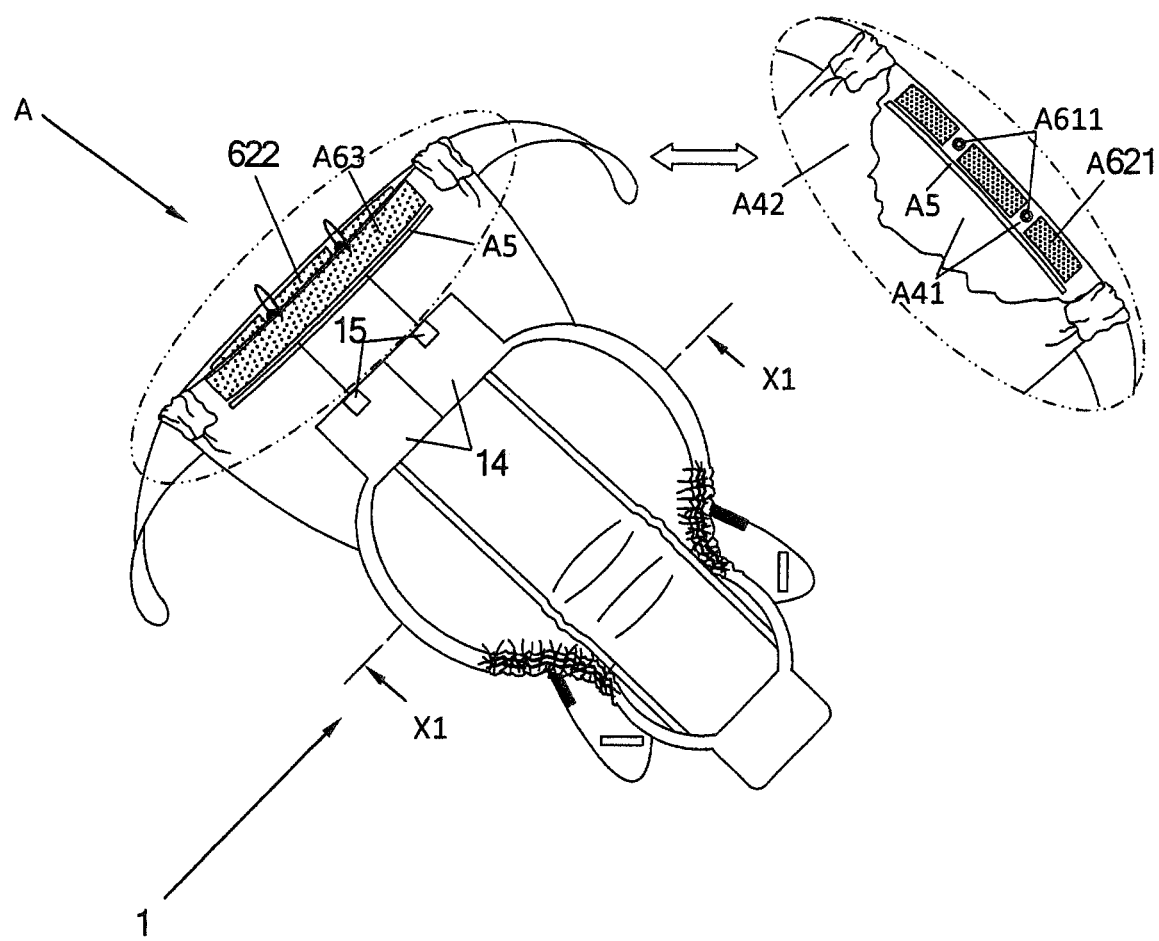

Referring to FIG. 2, a full-pad type absorbent article 2 of another embodiment is shown, wherein the left and right rear pulling sections 24 can be set in an upward direction into the rear opening A5 that has been pulled open or can be folded rearward and set, in a downward direction, into the rear clamp section A6 and then, male-female fasteners A61 are applied from opposite sides to attach to the hook-and-loop fasteners A62 for skidding prevention. The remaining parts are similar to those of the previous first embodiment.

Figures 1, 2, 3:
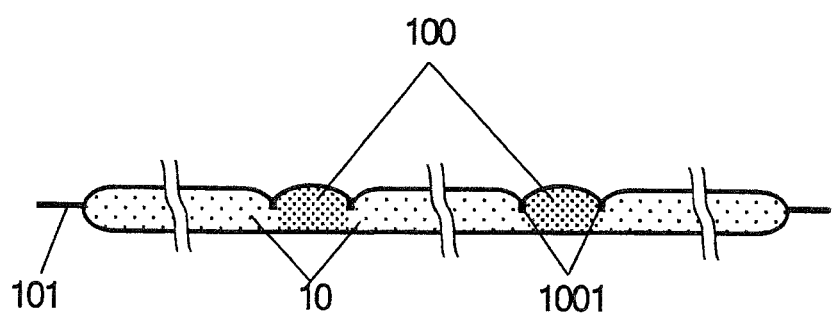

Referring to FIGS. 3-1 to 3-3, a partial-pad type absorbent article 3 of a different embodiment is shown, comprising an absorbent core layer 30 distributed on a rear hip zone 31 and a crotch zone 32, left and right rear pulling sections 34, and a front pulling section 36, wherein the crotch zone is fixed by a horizontal hot-pressed indentation line 371 that is spaced from an edge of a front end 30b by a distance of 2 cm and serving as a reference for a length L37, based on which rearward folding is made to form a folded stop portion 37, with each of left and right sides being fixed by a vertical hot-pressed indentation line 372. The front pulling section 36 comprises a planar surface formed of a portion of coupling film above the front end 30b of the absorbent core layer 30 and having a U-shaped notch 360 that allows for exposure of male generative organ and also allows for extension of a catheter 8, 9 therethrough to get contact with the anti-skidding glue, and two end portions 361 extending upward to be insertable through a front opening A11 and then folded downward for being clamped by a front clamping section A12, a shown in FIG. 3-3. The U-shaped notch has a bottom portion that, once lifted upward, would help prevent waste product from getting exposed during sitting up or taking activity. The remaining structure is the same as that of the first embodiment.

Figures 1, 2, 3, 4:
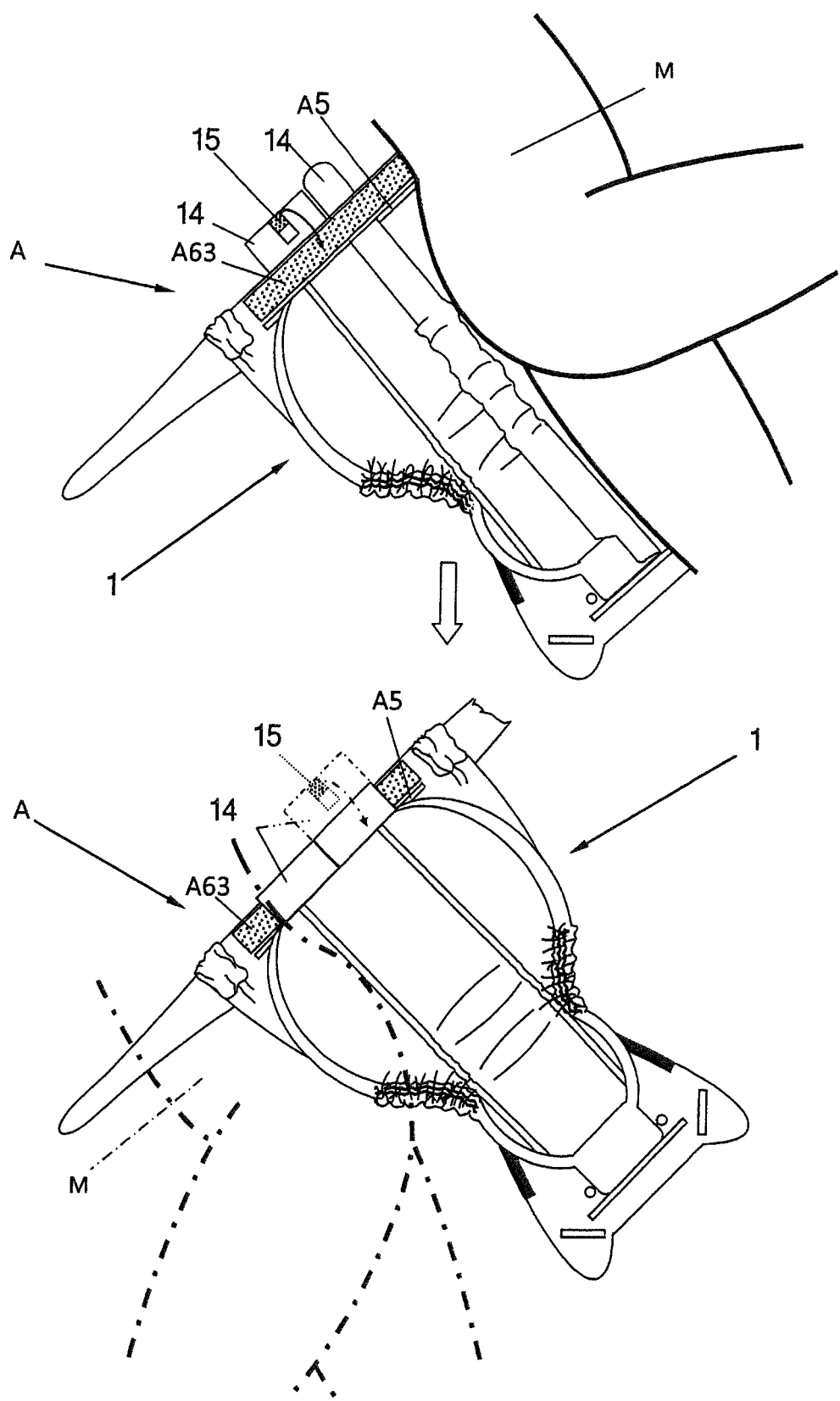

Referring to FIG. 4, a partial-pad type absorbent article 4 of a different embodiment is shown, wherein the left and right rear pulling sections 44 are similar to the counterparts of the second embodiment, while the remaining structure is the same as that of the third embodiment.

Figures 1, 2, 3, 4, 5:
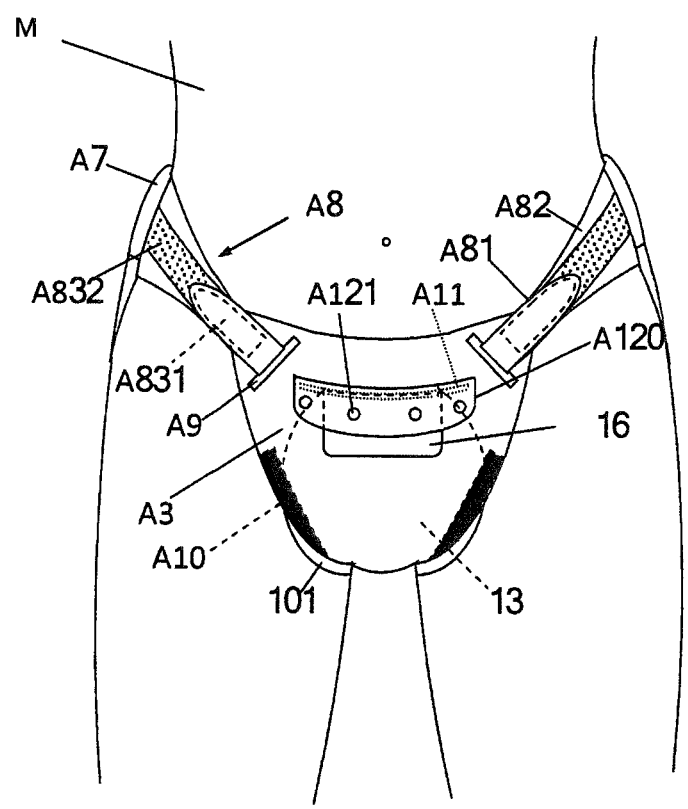

Referring to FIGS. 5-1 and 5-2, a partial-pad type absorbent article 5 of a different embodiment is shown, wherein a rear hip zone 51 is additionally provided with left and right back adhesive portions 58 adhesively attachable to a rear portion A1 and two end portions 561 of a front pulling section 56 are provided, on back side thereof, with adhesive portions 59 adhesively attachable to a front portion A3. Left and right rear pulling sections 54 are similar to those of the second embodiment (or the first embodiment), while the remaining structure is the same as that of the fourth embodiment.

Figures 1, 2, 3, 4, 5, 6:
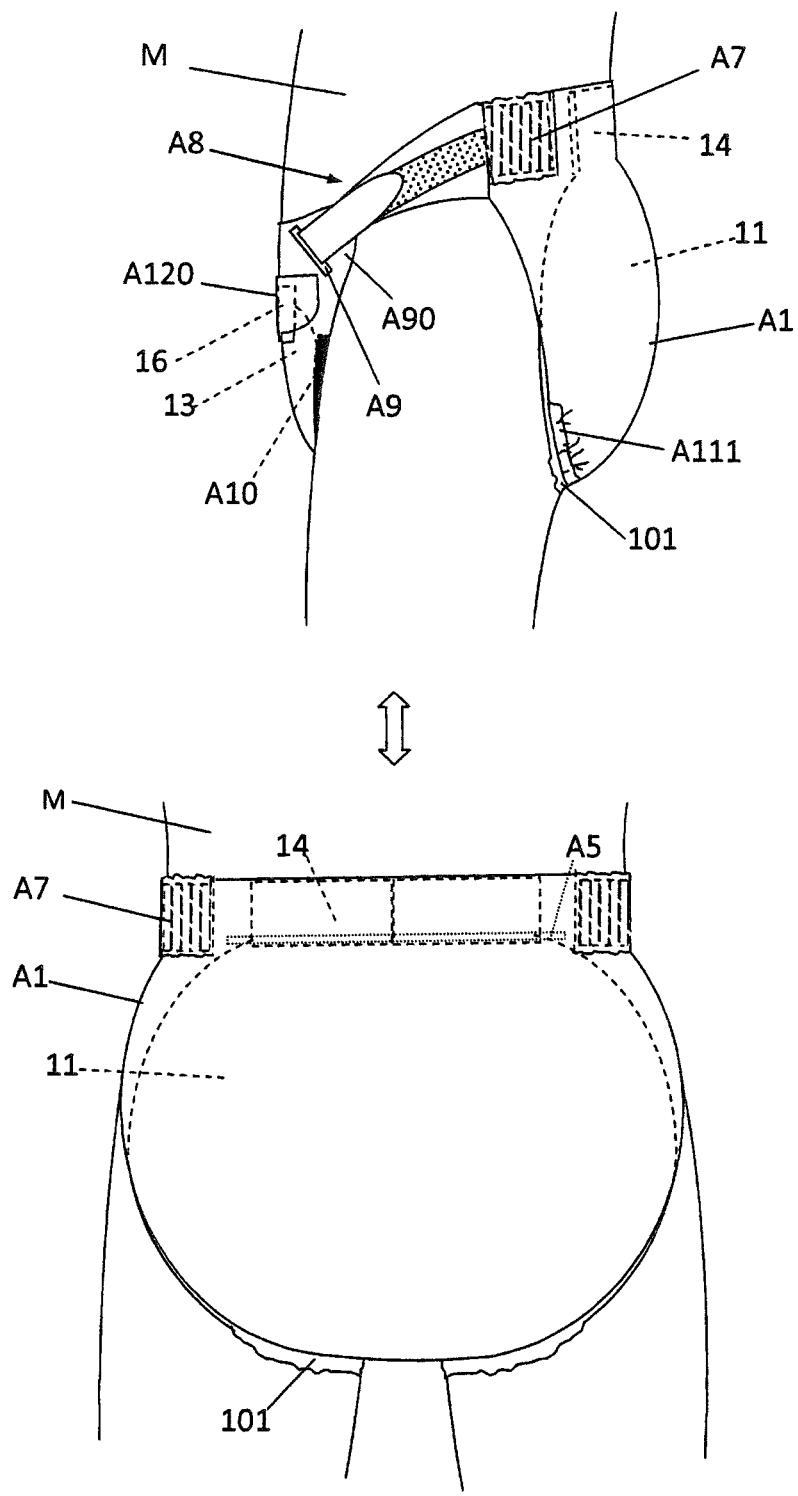
Figure 2:
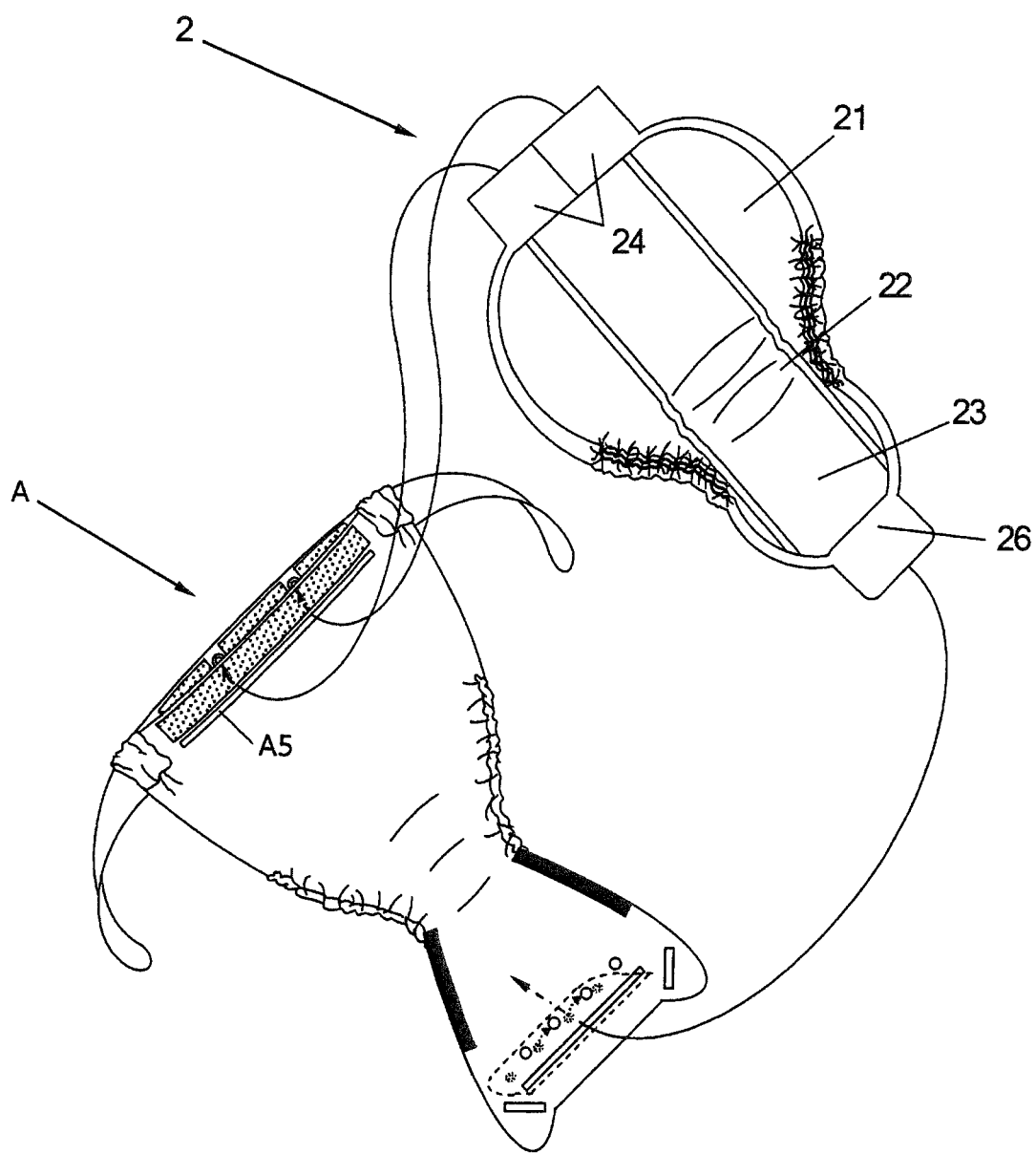
Figures 2, 3:
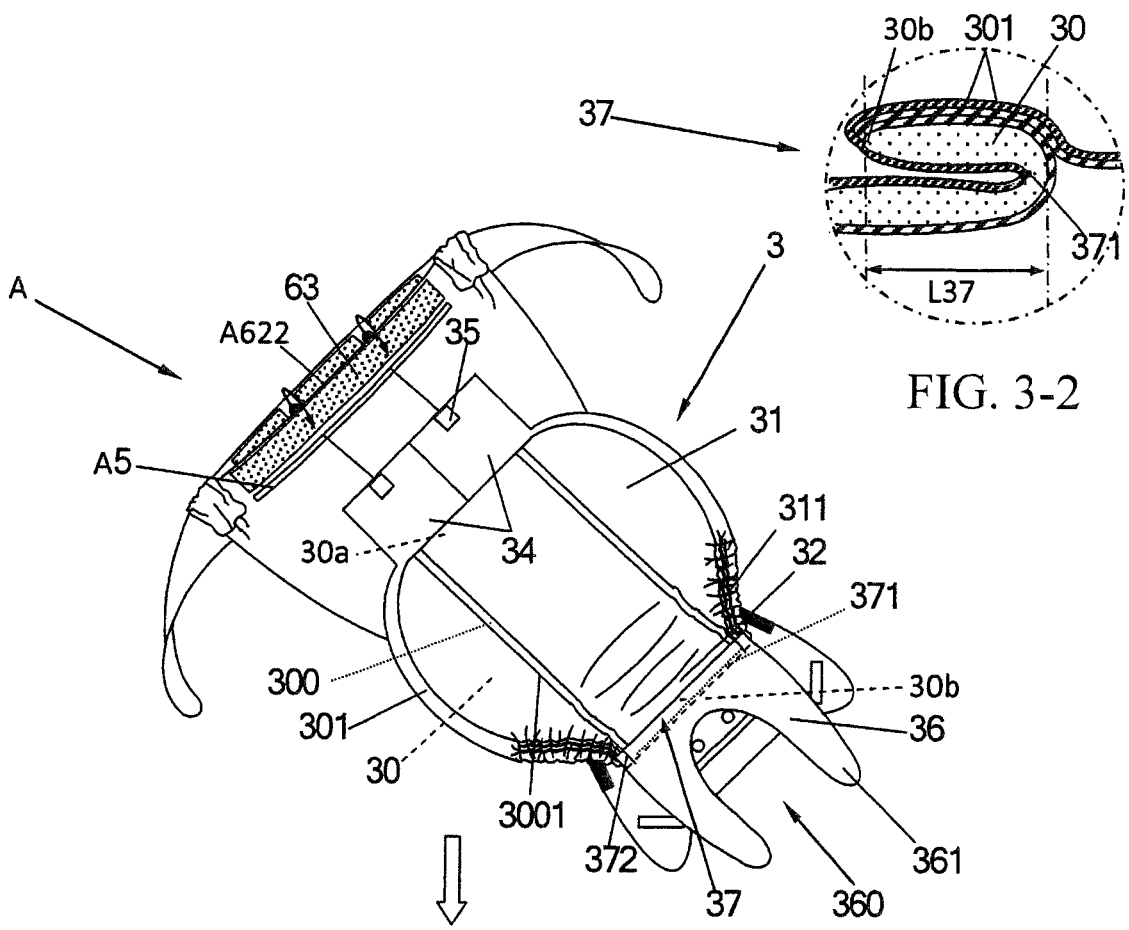
Figures 1, 3:
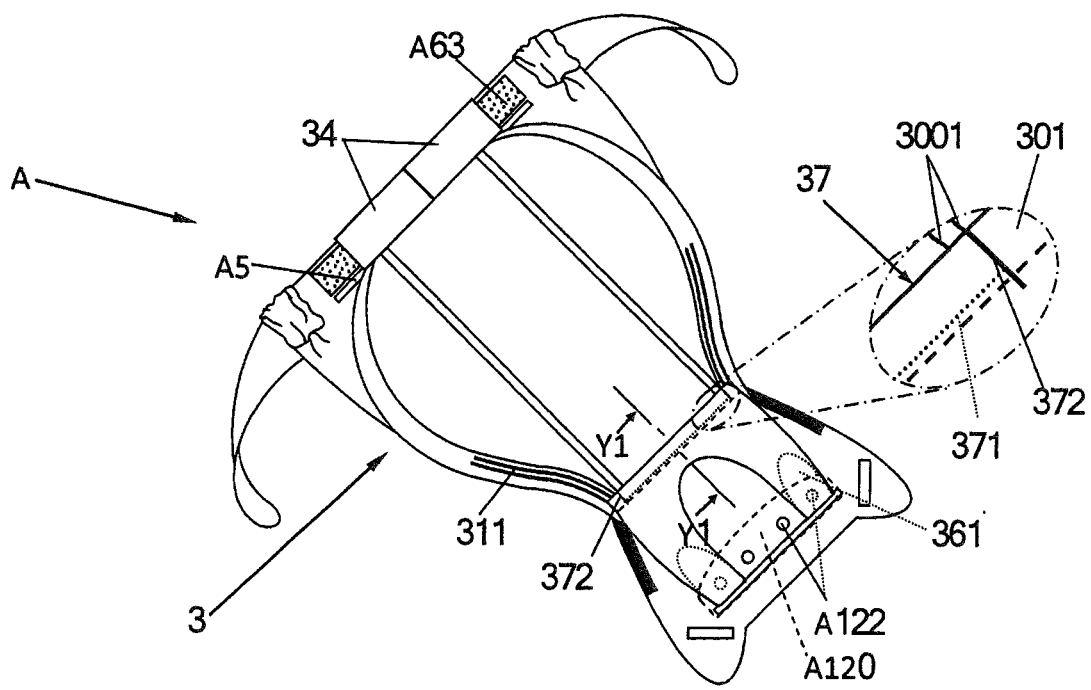
Figure 3:
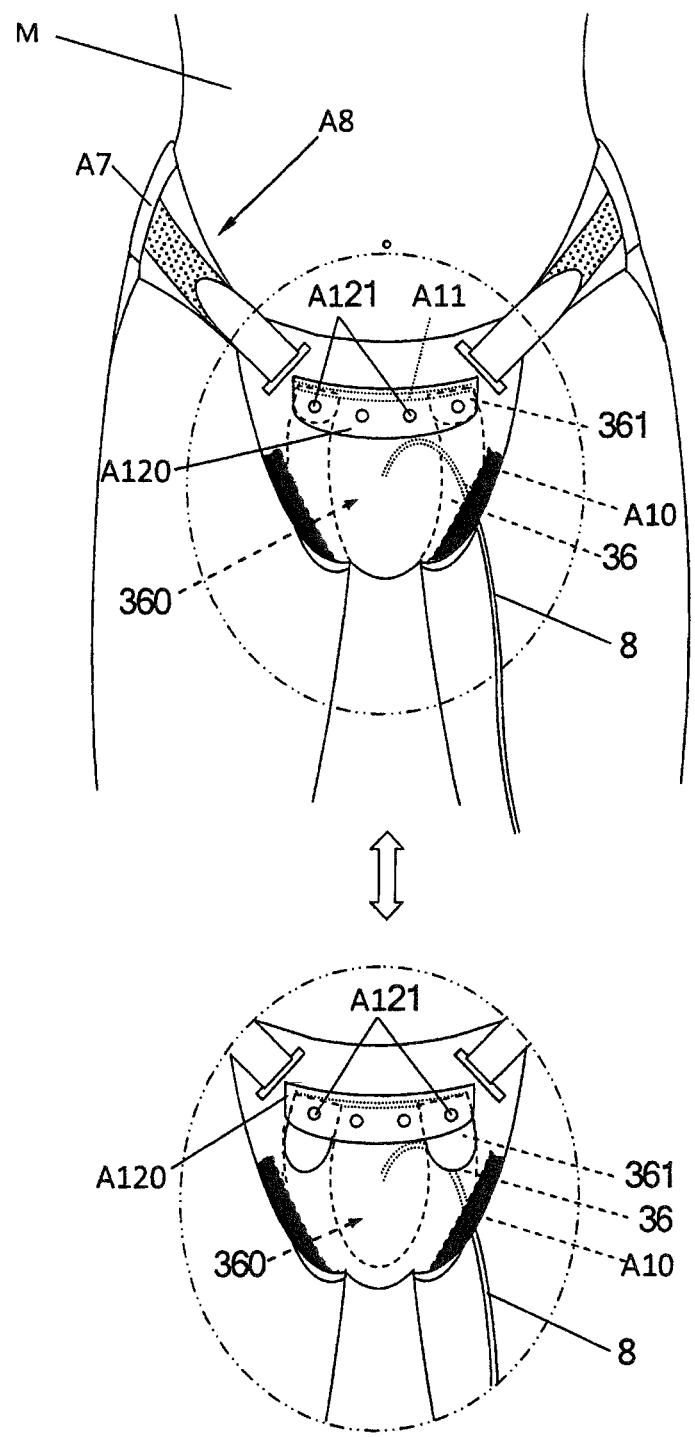
Figure 4:
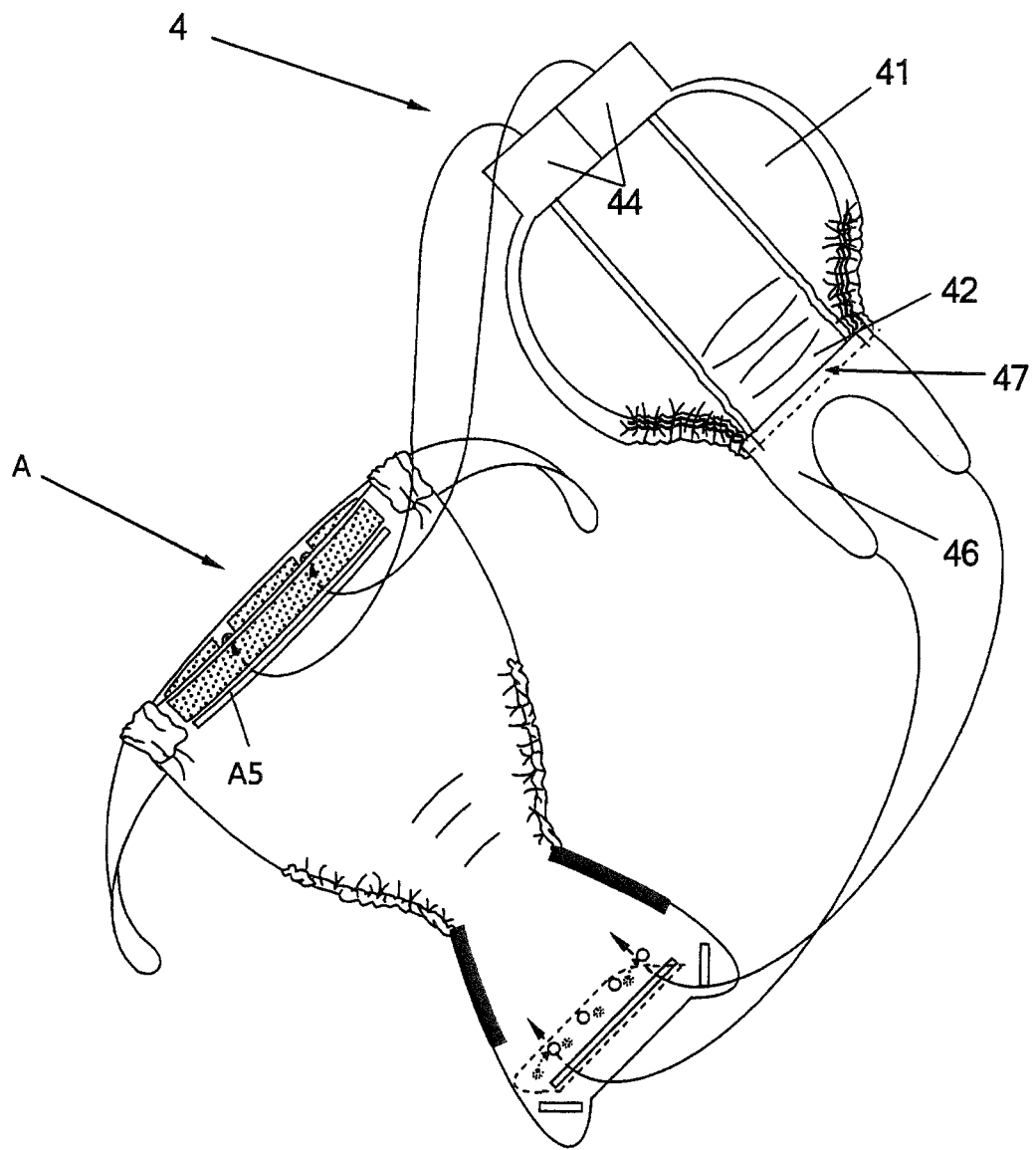
Figures 1, 5:
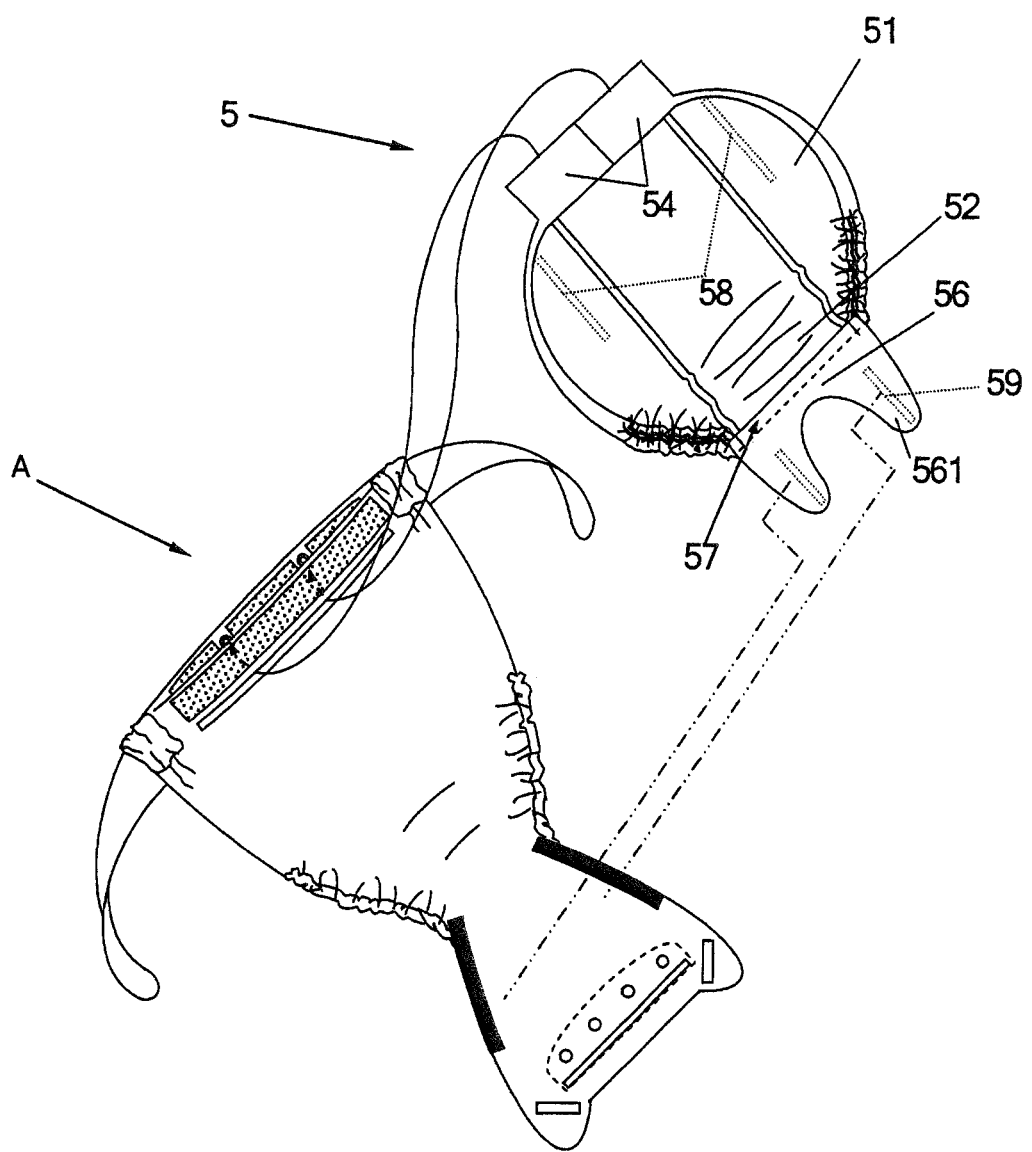
Figures 2, 5:
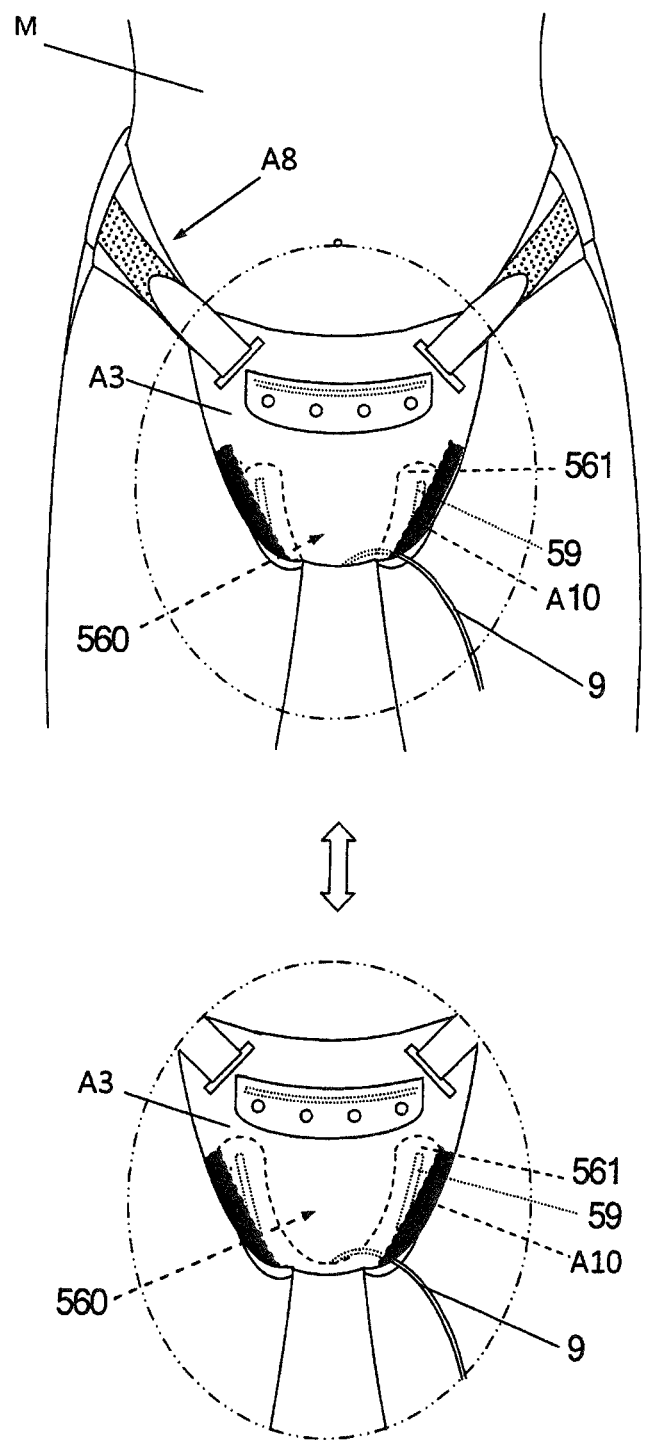
Figure 6:
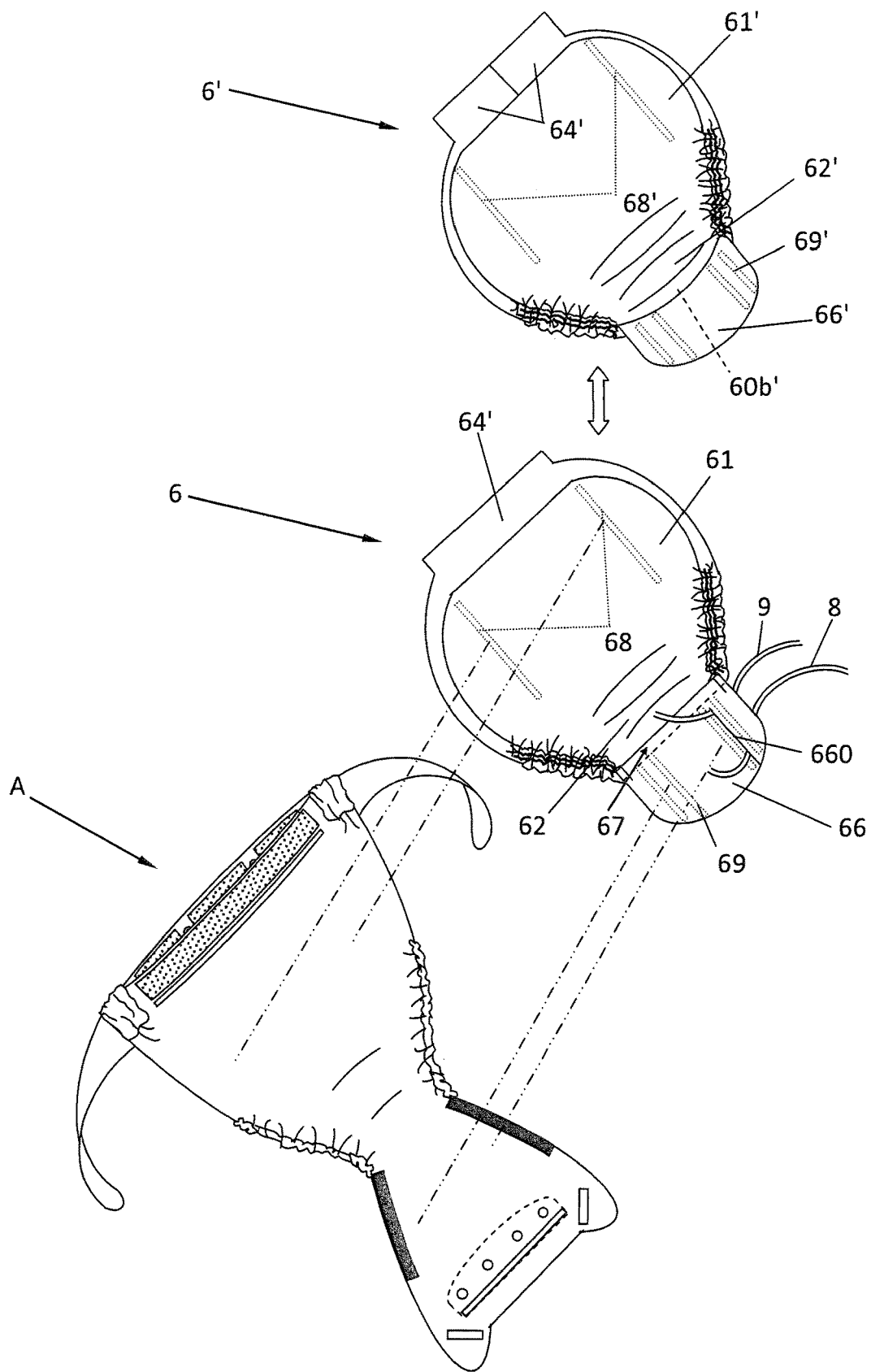

Referring to FIG. 6, a partial-pad type absorbent article 6 of a further embodiment is shown, wherein left and right back adhesive portions 68 are provided on a rear hip zone 61 for adhesively attachable, on two sides, to a front portion A3, and a single rear pulling section 64 can be clamped to provide secondary fixing. A front pulling section 66 is provided, in a vertically extending manner, at a location on an inner side thereof and adjacent to one of anti-skidding glue portions thereof, a cut-open slit 660 for extension of a male or female catheter 8, 9 therethrough and a plurality of back adhesive portions 69 adhesively attachable to a front portion A3 for fixing left and right sides of the cut-open slit. A modified partial-pad type absorbent article 6' comprises both left and right rear pulling sections 64' and left and right back adhesive portions 68' and has a front end 60b' that is provided with no folded stop portion. The front pulling section 66' comprises no slit or notch and is provided with a plurality of back adhesive portions 69'.

Figure 7:
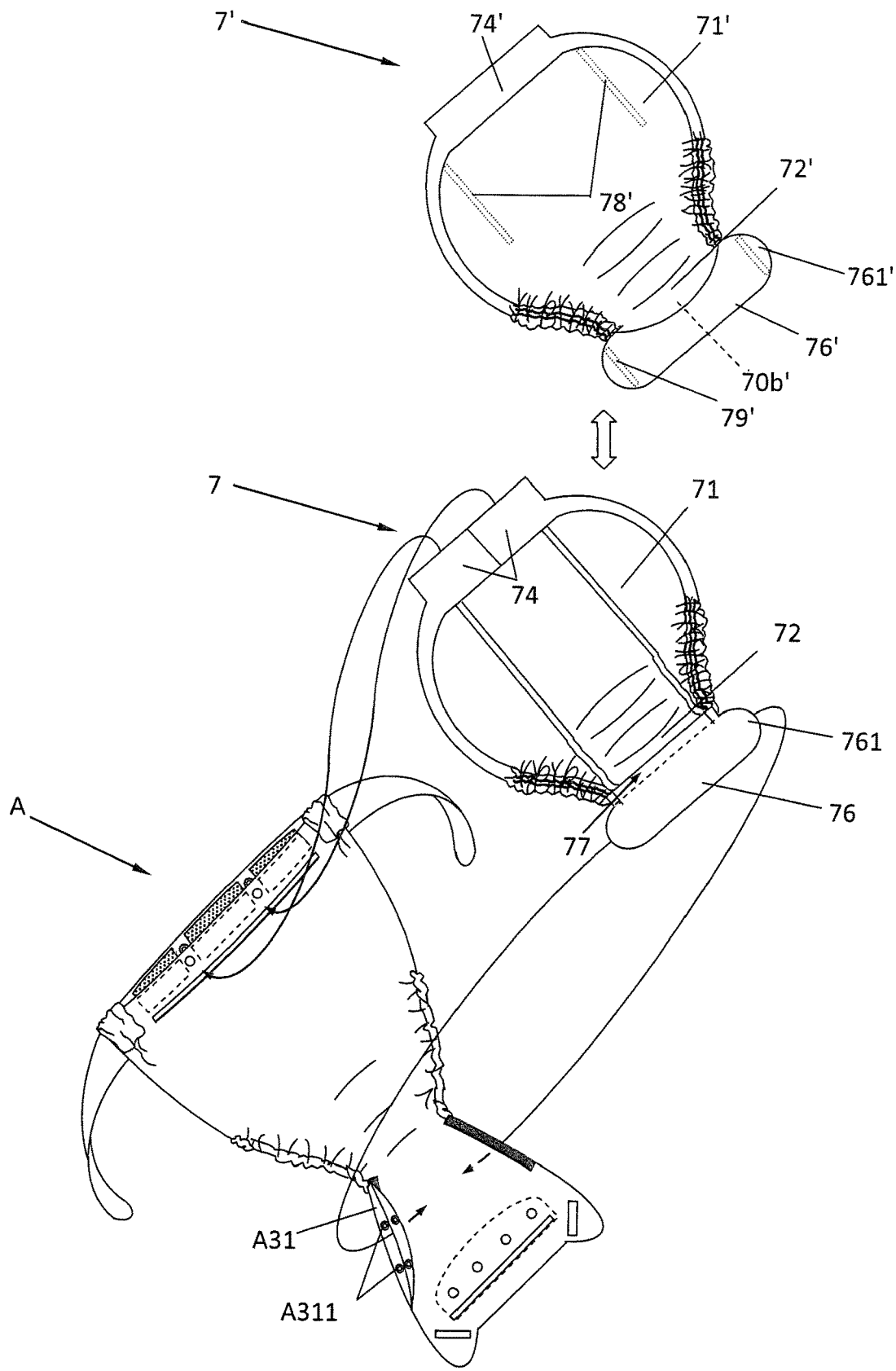
FIG. 7 is a schematic view demonstrating expansion of a partial-pad type absorbent article 7 and a holding and looping member according to a seventh embodiment, and also illustrating a modified absorbent article 7' for reference and comparison.

Referring to FIG. 7, a partial-pad type absorbent article 7 of yet a further embodiment is shown, wherein a front pulling section 76 is provided with left and right side wings 761, which are insertable into a side clamp section A30 and then fixed by a male-female fastener A311 without being exposed, and the remaining structure is similar to that of the fourth embodiment. A modified partial-pad type absorbent article 7' comprises a single rear pulling section 74' that can be clamped for secondary fixing and has a front end 70b' that comprises no folded stop portion. A front pulling section 77 has left and right side wings 761' that are provided with back adhesive portions 79' for adhesive fixing after being set into a side clamp section A30.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A material saving clothing, comprising:
   a repeatedly usable holding and looping member which comprises: a double-layered main body; an extendible/retractable section provided on each of a left end and a right end of a rear waist portion of the repeatedly usable holding and looping member; a pulling and holding band connected to each of outer ends of the extendible/retractable section, the pulling and holding band having a front segment which extends through a through hole formed in a front portion of the repeatedly usable holding and looping member, and the front segment to be pulled tightly and foldable rearward to get fastening engagement with a rear segment of the pulling and holding band, the rear segment of the pulling and holding band being widened in a direction toward the main body to a doubled width; a rear opening being provided under an internal layer between the extendible/retractable sections to allow left and right rear pulling sections of an absorbent article to be set therein and penetrating upward therethrough; a rear clamp section provided above the rear opening, the rear clamp section comprising female fastener parts of two horizontally arranged male-female fastens provided on the internal layer for coupling with male fastener parts of the two horizontally arranged male-female fastener provided on an external layer, and male portions of hook-and-loop fasteners respectively arranged between the two female fastener parts and opposite left and right sides thereof for respectively coupling with female portions of the hook-and-loop fasteners provided on the external layer for respectively clamping and pulling up the left and right rear pulling sections, the rear clamp section being covered, on a front side thereof, with a soft woven surface attachable to the attaching section of the left and right rear pulling sections; the front portion being provided with a front opening arranged horizontally and set at a location corresponding to a portion between the pubic bone and the belly button, the front opening which extends through the double layered main body comprising a front clamping section that comprises female fastener parts of a plurality of horizontally arranged male-female fasteners provided on an internal layer of a coupling lid that shields the front opening for corresponding to and coupling with male fastener parts of the male-female fasteners provided on the front portion to allow a front pulling section of the absorbent article to be pulled through the front opening and clamped and pulled up by the front clamping section; a shrinkage edge being formed on each of a left side and a right side by providing an elastic band to each of left and right sides of a lower part of the rear portion and associated left and right sides of a lower portion; the front portion, being provided on a left side and a right side of a lower part thereof, with a side clamp section that comprises a male-female fastener mounted to surfaces of the internal layer and the external layer that face each other for openably coupling therebetween and pulling up left and right side wings of the front pulling section of the absorbent article; the front portion being provided, on the internal layer at locations adjacent to each of a left lower edge and a right lower edge, with anti-skidding glue for preventing movement of a catheter; and
   an absorbent article, which is formed of a nonwoven surface layer, a waterproof bottom layer, and an absorbent core layer interposed therebetween, and has circumference along which a coupling film is formed, wherein a portion of the coupling film above a rear end of the absorbent core layer that is ¼ of a total waist circumference length is bisected into two equal parts respectively forming left and right rear pulling sections, a portion of the coupling film above a front end forming a planar front pulling section, an extendible/retractable edge, which is formed of an elastic band, being provided on a portion of the coupling film that is located on a lower part of each of left and right sides of the a hip zone and associated left and right sides of a crotch zone.

2. The material saving clothing according to claim 1, wherein the left and right rear pulling sections are each provided, on a front side thereof at a location adjacent to a middle of an upper edge thereof, with an adhering and attaching pad to be fit into the rear opening, extending upward therethrough, and folded frontward to attach back to the attaching section or the rear hip zone.

3. The material saving clothing according to claim 1, wherein the left and right rear pulling sections are positionable in an upward direction into the rear opening or, alternatively, are foldable rearward and positionable in a downward direction into the rear clamp section to be clamped and fixed.

4. The material saving clothing according to claim 1, wherein the absorbent core layer covers a range comprising the rear hip zone, the crotch zone, and a front belly zone to serve as a full-pad type absorbent article, the front pulling section having a width that is ⅛ of the total waist circumference length and a length sufficient to be clamped for frontward/rearward movements of the left and right rear pulling sections, and being withdrawn out through the front opening to be folded downward and clamped and fixed by the front clamping section.

5. The material saving clothing according to claim 4, wherein the crotch zone is provided, at a location adjacent to each of a left side edge and a right side edge thereof, with a tight core stop portion of the high density liquid absorbent core layer, which is of a width that is 1 cm and extend to the front end and the rear end, and the tight core stop portion is provided with a hot-pressed indentation line on each of left and right sides thereof.

6. The material saving clothing according to claim 1, wherein the absorbent core layer covers a range comprising the rear hip zone and the crotch zone to serve as a partial-pad type absorbent article, the crotch zone is fixed, at each of a left side edge and a right side edge thereof, by a horizontal hot-pressed indentation line that is spaced from an edge of a front end by a distance of 2 cm and serves as a reference for folding rearward to form a folded stop portion, each of left and right sides being fixed by a vertical hot-pressed indentation line, a front pulling section being provided above the crotch zone.

7. The material saving clothing according to claim 6, wherein the crotch zone is provided, at a location adjacent to each of a left side edge and a right side edge thereof, with a tight core stop portion of the high density liquid absorbent core layer, which is of a width that is 1 cm and extend to the front end and the rear end, and the tight core stop portion is provided with a hot-pressed indentation line on each of left and right sides thereof.

8. The material saving clothing according to claim 6, wherein the front pulling section comprises a U-shaped notch formed in a middle portion thereof and adapted to expose a male generative organ and two end portions being provided with a length sufficient to be clamped for frontward/rearward movements of the left and right rear pulling sections and being withdrawn out through the front opening to be folded downward and clamped and fixed by the front clamping section.

9. The material saving clothing according to claim 6, wherein the front pulling section comprises a U-shaped notch formed in a middle portion thereof and adapted to expose a male generative organ and two end portions being provided with back adhesive portions attachable to the front portion, the rear hip zone being provided with left and right back adhesive portions respectively attachable, on opposite sides, to the rear portion.

10. The material saving clothing according to claim 6, wherein the front pulling section is provided, at a location on an inner side of one of anti-skidding glue portions thereof, a cut-open slit adapt to allow for extension of a male or female catheter therethrough, the front pulling section being provided with a plurality of back adhesive portions adhesively attachable to the front portion for fixing left and right sides of the cut-open slit.

11. The material saving clothing according to claim 6, wherein the front pulling section is extended in leftward and rightward directions to form a planar surface having left and right side wings for being respectively positionable into side clamp sections to be clamped and fixed thereby.

12. The material saving clothing according to claim 1, wherein the absorbent core layer covers a range comprising the rear hip zone and the crotch zone to serve as a partial-pad type absorbent article, the front pulling section being provided with a plurality of back adhesive portions adhesively attachable to the front portion, the rear hip zone being provided with left and right adhesive portions adhesively attachable to the rear portion.

13. An absorbent article, which is formed of a nonwoven surface layer, a waterproof bottom layer, and an absorbent core layer interposed therebetween, and has circumference along which a coupling film is formed, wherein the absorbent core layer comprises a rear hip zone and a crotch zone to serve as a partial-pad type absorbent article, a portion of the coupling film that is located above a front end of the absorbent core layer forming a planar front pulling section, an extendible/retractable edge, which is formed of an elastic band, being provided on a portion of the coupling film that is located on a lower part of each of left and right sides of the a hip zone and associated left and right sides of the crotch zone, the rear hip zone being provided with left and right adhesive portions adhesively attachable, on opposite sides, to a rear portion of a holding and looping member that comprises a side clamp section.

14. The absorbent article according to claim 13, wherein the crotch zone is fixed, at each of a left side edge and a right side edge thereof, by a horizontal hot-pressed indentation line that is spaced from an edge of a front end by a distance of 2 cm and serves as a reference for folding rearward to form a folded stop portion, each of left and right sides being fixed by a vertical hot-pressed indentation line, and the front pulling section is provided, at a location on an inner side of one of anti-skidding glue portions thereof, a cut-open slit adapt to allow for extension of a male or female catheter therethrough, the front pulling section being provided with a plurality of back adhesive portions adhesively attachable to the front portion for fixing left and right sides of the cut-open slit.

15. The absorbent article according to claim 13, wherein the front pulling section is extended in leftward and rightward directions to form a planar surface having left and right side wings, with the left and right side wings being provided with back adhesive portions, for being respectively positionable into side clamp sections to be clamped and fixed thereby.

* * * * *